(12) United States Patent
Mazik

(10) Patent No.: US 8,513,420 B2
(45) Date of Patent: *Aug. 20, 2013

(54) AMINO-NAPHTHYRIDINE DERIVATIVES

(75) Inventor: Monika Mazik, Braunschweig (DE)

(73) Assignee: Monika Mazik, Braunschweig (DE)

( * ) Notice: Subject to any disclaimer, the term of this patent is extended or adjusted under 35 U.S.C. 154(b) by 575 days.

This patent is subject to a terminal disclaimer.

(21) Appl. No.: 12/531,996

(22) PCT Filed: Mar. 18, 2008

(86) PCT No.: PCT/EP2008/002160
§ 371 (c)(1),
(2), (4) Date: Jan. 7, 2010

(87) PCT Pub. No.: WO2008/113558
PCT Pub. Date: Sep. 25, 2008

(65) Prior Publication Data
US 2010/0113505 A1    May 6, 2010

(30) Foreign Application Priority Data

Mar. 19, 2007 (EP) .................................. 070055651

(51) Int. Cl.
*A61K 31/44* (2006.01)
*C07D 471/02* (2006.01)

(52) U.S. Cl.
USPC .......................................... 546/122; 514/300

(58) Field of Classification Search
USPC .................. 544/235; 514/248, 300; 546/122
See application file for complete search history.

(56) References Cited

U.S. PATENT DOCUMENTS

| 5,622,724 A | 4/1997 | Bryce-Smith |
| 2004/0044207 A1 | 3/2004 | Anthony et al. |
| 2005/0182085 A1 | 8/2005 | Defossa et al. |
| 2011/0136840 A1 * | 6/2011 | Mazik et al. ................. 514/275 |

FOREIGN PATENT DOCUMENTS

| EP | 1 695 974 | 8/2006 |
| EP | 1 714 966 | 10/2006 |
| EP | 1714966 | 10/2006 |
| WO | 0050424 | 8/2000 |
| WO | WO 00/50424 | 8/2000 |
| WO | 0170742 | 9/2001 |
| WO | WO 01/70742 | 9/2001 |
| WO | 2007022946 | 3/2007 |
| WO | WO 2007/022946 | 3/2007 |

OTHER PUBLICATIONS

West, Anthony R., Solid State Chemistry and its Applications, Wiley, New York, 1988, pp. 358 & 365.*
M. Wozniak, et al,. "Reactions of 2-Chloro-1, 8-Naphthyridine with Some Nucleophiles", Polish Journal of Chemistsry, vol. 55, 1981, pp. 2427-2437.

* cited by examiner

*Primary Examiner* — Janet Andres
*Assistant Examiner* — Heidi Reese
(74) *Attorney, Agent, or Firm* — Whitham Curtis Christofferson & Cook, PC

(57) ABSTRACT

The present invention relates to new compounds having an amino-naphthyridine group. In particular, the present invention relates to new compounds, its stereoisomers and pharmaceutically acceptable salts or solvates thereof having a first unit (moiety) selected from the group of a phenyl derivative, a biphenyl derivative or a diphenyl alkane derivative and at least one amino-naphthyridine group linked with the first unit via a linking group. In specific embodiments, the present invention relates to compounds having a phenyl derivative unit and three amino-naphthyridine groups bound to the phenyl derivative unit via a linking group as well as salts or solvates thereof, in particular, pharmaceutically acceptable salts or solvates thereof. Further, the present invention relates to pharmaceutical compositions comprising said compounds. The compounds are particularly useful for treating or preventing infections, like viral infections.

15 Claims, 6 Drawing Sheets

Scheme 3 a) NaNO₂, 20 % HCl, KI; b) PdCl₂(dppf), KOAc/DMF, 80 °C, 2h; c) 2 equiv of 8, PdCl₂(dppf), CsF, 80 °C, 12 h; d) LiBH₄, THF; e) 48 % HBr; f) CH₃CN/THF, K₂CO₃, 48h; g) H₃PO₄, 90 °C, 4h; h) CH₃OH, 10 % HCl

Scheme 4 a) 20 % Oleum; b) CH₃OH, HCl; c) LiBH₄, THF; d) 48 % HBr; e) CH₃CN/THF, K₂CO₃, 48h; f) H₃PO₄, 90 °C, 4h; g) CH₃OH, 10 % HCl Scheme 5

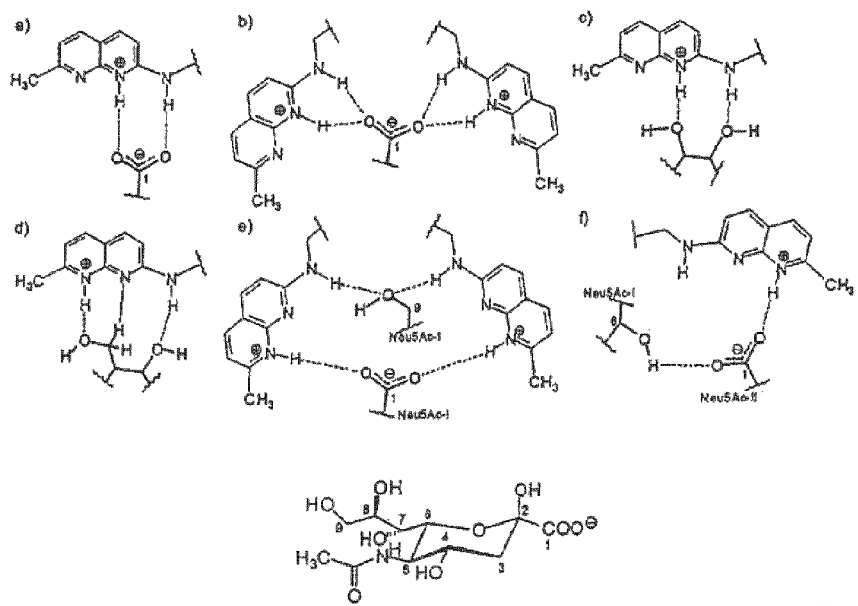

Figure 6. Examples of neutral/charge-reinforced hydrogen bonds and ion pairing found by molecular modeling studies in the complexes formed between receptor 4b (N1- or N8-protonated) and (a,b,e,f) Neu5Ac (Neu5Ac-I/II: two Neu5Ac molecules involved in the formation of 1:2 receptor-sugar complexes), or (c,d) β-D-maltose (1:1 receptor-sugar complexes). MacroModel V.8.5, OPLS-AA force field, MCMM, 50000 steps.

AMINO-NAPHTHYRIDINE DERIVATIVES

The present invention relates to new compounds having an amino-naphthyridine group. In particular, the present invention relates to new compounds, its stereoisomers and pharmaceutically acceptable salts or solvates thereof having a first unit (moiety) selected from the group of a phenyl derivative, a biphenyl derivative or a diphenyl alkane derivative and at least one amino-naphthyridine group linked with the first unit via a linking group. In specific embodiments, the present invention relates to compounds having a phenyl derivative unit and three amino-naphthyridine groups bound to the phenyl derivative unit via a linking group as well as salts or solvates thereof, in particular, pharmaceutically acceptable salts or solvates thereof. Further, the present invention relates to pharmaceutical compositions comprising said compounds. The compounds are particularly useful for treating or preventing infections, like viral infections.

BACKGROUND

Naphthyridine derivatives are known in the art and have been described to display various properties. For example, 1,8-naphthyridines have been described to function as CFR receptor antagonists, see EP 1 695 974. These naphthyridines acting as CFR receptor antagonists may represent novel antidepressant and/or anxiolytic drugs that may be useful in the treatment of the neuropsychiatric disorders manifested in hypersecretion of CRF. In US 2005/0182085 naphthyridine derivatives and physiologically tolerated salts and physiologically functional derivatives thereof are described which are beneficial in reducing blood glucose or having disturbances of lipid and carbohydrate metabolism, like the metabolic syndrome.

Further, anti-fungal, anti-viral and anti-bacterial properties of various naphthyridine derivatives are known. For example, in Bedard et al., Antimicrobialagents and Chemotherapy, April 2000, pages 929 to 937, the properties of a series of 1,6-naphthyridine and 7,8-diisochinoline derivatives exhibiting potent activity against human cytomegaloma virus have been described. Furthermore, naphthyridine derivatives having anti-viral activity are described in EP 1 714 966, WO 01/70742, US 2004/044207 and WO 00/50424, respectively.

However, there is still a continuous need for compounds useful as active ingredients of pharmaceutically active and specific pharmaceuticals.

The present invention addresses the need for further compounds based on naphthyridine and its derivatives. That is, the present invention addresses to provide new effective and specific compounds based on naphthyridine and its derivatives. The invention provides new compounds composed of a so called spacer unit (first unit) and at least one naphthyridine unit. These molecules would be of beneficial use in a variety of applications, including treating or preventing infections, in particular, viral, bacterial or fungal infection. The present invention fulfils these and other needs.

SUMMARY OF THE INVENTION

The present invention relates to the provision of new compounds composed of a spacer unit A and at least one amino-naphthyridine unit B bound to the spacer unit via a linker moiety, in particular, a methylene group as well as salts or solvates thereof, which are particularly useful in therapeutic or prophylactic treatment of various diseases, disorders or conditions. The present inventors recognized that the acyclic amino-naphthyridine based molecules are artificial receptors for carbohydrate recognition. In particular, the molecules of the present invention are able to bind selectively and transiently or permanently to e.g. N-acetylneuraminic acid (Neu5Ac). N-acetylneuraminic acid is known to be overexpressed on the cell surface of tumor cells and, in addition, sialic acids and derivatives, like Neu5Ac, are frequently used as a recognition site for viruses. Thus, in a further aspect, the present invention relates to pharmaceuticals containing the compounds of the present invention. These pharmaceuticals are particularly useful for preventing or treating infections, in particular, viral, parasitic, bacterial and fungal infections.

The newly developed compounds composed of the spacer unit and the amino-naphthyridine derivative units are able to interact specifically with neutral and ionic (anionic or cationic) sugar molecules like Neu5Ac which is a representative of an anionic sugar. The interaction involves hydrogen-bonding, CH-π-interactions, ion pairing and ionic hydrogen-bonding.

Thus, these new molecules are artificial receptors for the recognition of neutral and ionic sugar molecules, like Neu5Ac, allowing transient or permanent masking or blocking of sugar molecules, thus, preventing recognition and docketing of e.g. virus particles to host cells. That is, the new compounds may bind to its ligands present either on the surface of virus particles or other invaders, on host cells or present in the body fluid or extracellular space of an individual preventing interaction between said ligands and other molecules present on host cells, invaders, like virus, bacteria or parasites, the body fluid or the extracellular space.

Particular preferred, the amino-naphthyridine is a 2-amino-1,8-naphthyridine which may be substituted. In a preferred embodiment the spacer unit is a phenyl derivative of the general formula II.

The pharmaceutical composition comprising the compounds according to the present invention in effective amounts, optionally, together with pharmaceutically acceptable excipient can be used for the treatment or prevention of various diseases, disorders and conditions, in particular, infection diseases and cancer. Finally, the present invention relates to methods for treating infectious diseases or cancer comprising administering the compounds of the present invention to patients in need thereof.

DETAILED DESCRIPTION OF THE INVENTION

The invention relates to compounds of the general formula I including stereoisomers and salts or solvates thereof.

$$A\text{-}(CH_2\text{—}B)_n \quad (I)$$

wherein
A is
i) a phenyl derivative of the general formula (II)

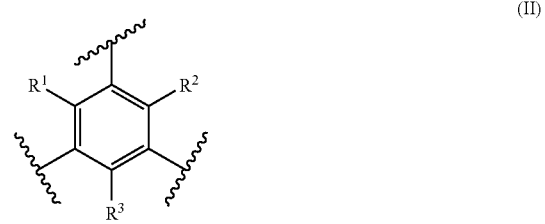

wherein each of $R^1$, $R^2$ and $R^3$ being independently hydrogen or a $C_1$-$C_6$ alkyl group, a $C_1$-$C_6$ alkoxy group, a hydroxyl group or a halogen with the proviso that at least one of $R^1$, $R^2$ or $R^3$ is not hydrogen;

ii) a biphenyl derivative of the general formula (III)

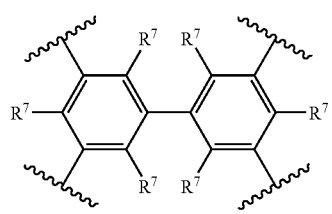

(III)

with each $R^7$ being independently a hydrogen or a $C_1$-$C_6$ alkyl group, a $C_1$-$C_6$ alkoxy group, a hydroxyl group or a halogen;

iii) a diphenyl alkane derivative of the general formula (IV)

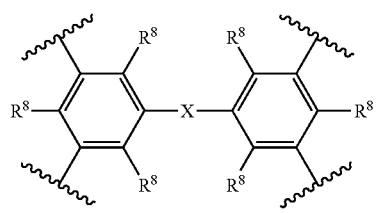

(IV)

with each $R^8$ being independently a hydrogen or a $C_1$-$C_6$ alkyl group, a $C_1$-$C_6$ alkoxy group, a hydroxyl group or a halogen; X is a $C_1$-$C_6$ alkyl group, in particular, a methylen group; B is independently an amino-naphthyridine group of the general formula (V), (VI), or (VII)

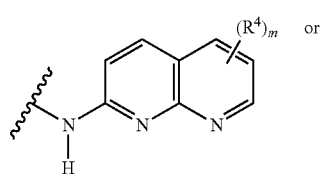

(V)

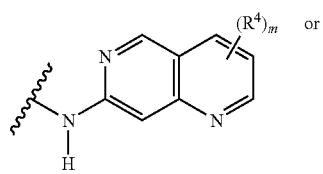

(VI)

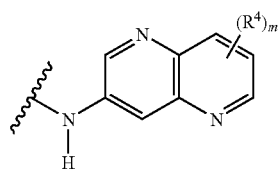

(VII)

wherein each $R^4$ is independently a hydrogen, a $C_1$-$C_6$ alkyl group, hydroxyl group, $C_1$-$C_6$ alkoxy group, halogen or $NR^{10}R^{11}$ with $R^{10}$ and $R^{11}$ being independently hydrogen or a $C_1$-$C_6$ alkyl group, and m is an integer of 2 to 5, and n is an integer of 1, 2, or 3 if A is a phenyl derivative of formula (II) or n is 1, 2, 3, or 4 if A is (III) or (IV).

B may be identical or different from each other. Preferably, if n is $\geq 2$ all B are identical.

A preferred embodiment of the present invention relates to compounds wherein B is independently an amino-naphthyridine group of the general formula (Va), (VIa), or (VIIa)

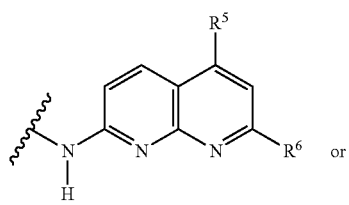

(Va)

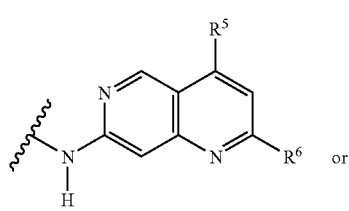

(VIa)

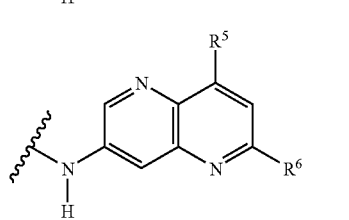

(VIIa)

wherein $R^5$ or $R^6$ being independently a $C_1$-$C_6$ alkyl group, hydroxyl group, $C_1$-$C_6$ alkoxy group, halogen or $NR^{10}R^{11}$ with $R^{10}$ and $R^{11}$ being independently hydrogen or a $C_1$-$C_6$ alkyl group.

In a preferred embodiment the compound of the general formula I is a physiologically tolerated and pharmaceutically acceptable salt or solvate.

The invention relates to compounds of the formula I in the form of their racemates, racemic-mixtures and pure enantiomers and their diastereomers and mixtures thereof.

Pharmaceutically acceptable salts are particularly suitable for medical applications because their solubility in water is greater than that of the initial or basic compounds. Suitable pharmaceutically acceptable acid addition salts of the compounds of the invention are salts of inorganic acids such as hydrochloric acid, hydrobromic, phosphoric, metaphosphoric, nitric and sulphuric acid, and or organic acids, such as, for example, acetic acid, benzene-sulfonic, benzoic, citric, ethanesulfonic, fumaric, gluconic, glycolic, inothionic, lactic, lactobionic, maleic, malic, methanesulfonic, succinic, p-toluelenesulfonic and tartaric acid.

Within the scope of the present invention also salts with a pharmaceutically unacceptable anion are contemplated as well as the basic compounds. These salts with a pharmaceutically unacceptable anion may be useful as intermediates for the preparation or proliferation of pharmaceutically acceptable salts and/or for use in non-therapeutics, for example in vitro applications.

According to the present invention, the alkyl or alkoxy residues in the substituents $R^1$, $R^2$, $R^3$, $R^4$, $R^5$, $R^6$, $R^7$, $R^8$, $R^{10}$, and $R^{11}$ may be both straight-chain and branched. Optionally, the alkyl or alkoxy residues may be substituted; in particular, substitution may be present with a hydroxyl group, halogen, nitro group or $C_1$-$C_6$ alkoxy group.

If residues or substituents may occur more than once in the compounds of the formula I, they may all, independently of one another, have the stated meanings and be identical or different.

In a preferred embodiment the spacer unit is a phenyl derivative of the general formula (II)

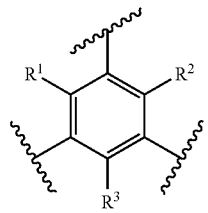

(II)

with each $R^1$, $R^2$ and $R^3$ being independently hydrogen or a $C_1$-$C_6$ alkyl group, a $C_1$-$C_6$ alkoxy group, a hydroxyl group or a halogen with the proviso that at least one of $R^1$, $R^2$ and $R^3$ is not a hydrogen. In a particular preferred embodiment the substituents $R^1$, $R^2$ and $R^3$ are independently an alkyl group selected from the group of methyl, ethyl, propyl or butyl. In a more preferred embodiment substituents, $R^1$, $R^2$ and $R^3$ are a methyl or ethyl group, preferably $R^1$, $R^2$ and $R^3$ are identical.

In a particularly preferred embodiment the spacer unit is a phenyl derivative with $R^1$, $R^2$ and $R^3$ being a methyl or ethyl group, the amino-naphthyridine unit is a 2-amino-1,8-naphthyridine unit with $R^6$ is methyl and $R^5$ is hydrogen. In another particularly preferred embodiment $R^1$, $R^2$, $R^3$ are a methyl or ethyl group and $R^5$ and $R^6$ are a methyl group.

Another preferred embodiment relates to compounds wherein the spacer unit is a biphenyl derivative of the general formula (III) with each $R^7$ being independently a hydrogen or $C_1$-$C_6$ alkyl group, a $C_1$-$C_6$ alkoxy group, a hydroxyl group or a halogen. Particularly preferred, the $C_1$-$C_6$ alkyl group is a methyl, ethyl, propyl or butyl group, whereby each $R^7$ may have the same meaning or may be different. In particularly preferred embodiments, each $R^7$ is independently hydrogen, methoxy, hydroxyl or methyl group. Specific embodiments of the compounds according to the present invention are compounds wherein each $R^7$ is independently methyl or ethyl group and $R^6$ is methyl, $R^5$ is hydrogen or a methyl group and the amino-naphthyridine group is a 2-amino-1,8-naphthyridine.

In addition, in another embodiment of the present invention the spacer unit is a diphenyl alkane moiety of the general formula (IV) where the alkane X is a $C_1$-$C_6$ alkylene group, preferably a methylene or ethylene group. Said diphenyl alkane derivative may be substituted with substituents $R^8$ where each $R^8$ is independently hydrogen, $C_1$-$C_6$ alkyl group, $C_1$-$C_6$ alkoxy group, hydroxyl group or a halogen. Preferably, each $R^8$ is independently a hydrogen, a methyl, ethyl, hydroxyl, methoxy or ethoxy group and, preferably, all $R^8$ are identical.

That is, another preferred embodiment relates to a compound of the general formula I wherein A is a diphenyl methane derivative of the general formula (IV) wherein $R^8$ is methyl, $R^6$ of the 2-amino-1,8 naphthyridine moiety is methyl and $R^5$ is hydrogen or methyl.

At least one amino-naphthyridine group of the general formulas (V), (VI), or (VII), in particular, of general formulas (Va), (VIa) or (VIIa) may be linked via the methylene group with the spacer molecule. That is, n is an integer of 1, 2 or 3 if the spacer moiety A is a phenyl derivative of formula (II) or n is an integer of 1, 2, 3, or 4 if A is a biphenyl derivative of general formula (III) or a diphenyl alkane derivative of general formula (IV).

Particularly preferred embodiments are shown in FIGS. 1 to 5.

As used herein, the following definitions will apply unless otherwise indicated:

"Therapeutically effective amount" means a quantity of the compound which is effective in treating the named disorder or condition.

The term "pharmaceutical composition" means a composition suitable for pharmaceutical use in a subject or an individual including an animal or human. A pharmaceutical composition generally comprises an effective amount of an active agent and a carrier, including e.g. a pharmaceutically acceptable carrier.

A "prophylactic treatment" is a treatment administered to a subject or an individual who does not display signs or symptoms of a diseases, pathology, or medical disorder, or displays only early signs of symptoms of disease, pathology or disorders, such that the treatment is administered for the purpose of diminishing, preventing, or decreasing the risk of developing the disease, pathology or medical disorder.

A "therapeutic treatment" is a treatment administered to a subject or an individual who display symptoms or signs of pathology disease, or disorder in which treatment is administered into the subject for the purpose of diminishing or eliminating those signs or symptoms of pathology, disease or disorder.

As used herein, the term "disease", "disorder", "pathology" and "condition" relates to infectious diseases, cancer, tumors or other disease involving binding or recognition of N-acetylneuraminic acid, other sialic acids, or carbohydrates in general. In particular, the disease, disorders, pathology and conditions include but are not limited to bacterial, fungal and viral infections, such as hepatitis B virus, hepatitis C virus, Human Immunodeficiency Virus, FIV influenza, coronavirus, Flavivirus, RSV as well as several others, such as Sendai, Newcastle disease, and polyoma viruses.

As used herein, the term "individual", "patient" or "subject" which is used herein interchangeably refers to an individual or a subject in need of the therapy or prophylaxis. The term "subject", "patient" or "individual" as used herein includes, but is not limited to an organism, a mammal including e.g. a human, a non-human primate (e.g. baboon, monkey), or non-human mammals.

As used herein, the term "carrier" refers to a diluent, adjuvant, excipient or vehicle.

The term "derivative" refers to compounds derived or obtained from another compound and containing essential elements of the parent substance.

The compounds according to the present invention can also be administered in combination with further active ingredients. That is, the pharmaceutical composition according to the present invention may comprise further active ingredients.

The amount of a compound or formula I necessary to achieve the desired biological effect depends on a number of factors the skilled person is well aware of. These factors include but not limited to the specific compounds chosen, the intended use, the mode of administration and the clinical condition of the patient. The pharmaceutical composition of the invention can be produced by one of the known pharmaceutical methods, which essentially consists of mixing the ingredients with pharmacologically acceptable carriers and/or excipient.

Formulations and Derivatives of Administration

The pharmaceutical composition according to the present invention containing the compounds of the general formula I are typically administered in a formulation that includes one or more pharmaceutically acceptable carriers or excipients. Such pharmaceutical compositions may be prepared in a manner known per se in the art to result in a pharmaceutical that is sufficiently storagestable and is suitable for administration to humans or animals.

Pharmaceutical acceptable carriers or excipients means a carrier or excipient that at the dosages and concentrations employed does not cause any untoward effects in the patients to whom it is administered. Such pharmaceutically acceptable carriers and excipients are well known in the art (e.g. see Remington's Pharmaceutical Sciences, 18th Edition, A. R. Genaro Ed. Mack, Publishing Company (1990), Handbook of Pharmaceutical Excipients, 3rd Edition, A. Kibbe, Ed. Pharmaceutical Press. 2000).

As indicated before, the term "carrier" or "excipient" refers to a carrier, diluent, adjuvant, excipient or vehicle with which the active ingredient is administered. Such pharmaceutical carriers can be sterile liquid, such as water and oils including those of petroleum, animal, vegetable or synthetic origin, such as peanut oil, soybean oil, mineral oil, sesame oil and the like. Water is a preferred carrier when the pharmaceutical composition is administered intravenously. Saline solutions and glycerol solutions can also be employed as liquid carriers, particularly for injectable solutions.

Suitable pharmaceutical excipient include starch, gelatine, malt, rice, fluor, chalk silica gel, sodium stereate, glycerol monostereate, talc, sodium chloride, dried skim milk, glycerol, propylene, glycol, water, ethanol and the like. Pharmaceutical excipients of the sugar type are less preferred due to possible interaction with the active ingredient. The composition if desired, can also contain minor amounts of wetting or emulsifying agents, or pH buffering agents. These compositions can take the forms of solutions, suspensions, emulsion, tablets, pills, capsules, powders, sustained-release formulations and the like. The composition can be formulated as a suppository with traditional binders and carriers such as glycerides. Oral formulations can include standard carriers, such as pharmaceutical grades of starch, sodium stereate, cellulose, magnesium, carbonate etc. Again, carriers based on sugars are less preferred due to possible interaction with the active principle.

The compounds according to the present invention may be also be a component of a pharmaceutical composition provided in a formulation suitable for parentaral administration, in particular, in subcutaneous, intravenous, intradermal or intramuscular administration.

As noted before, the pharmaceutical composition may be adapted for intravenous administration to human beings. Typically, compositions for intravenous administrations are solutions in sterile isotonic aqueous buffer. Where necessary, the composition may also include a solubilizing agent and a local anaesthetic, such as lidocaine to ease pain at the side of injection.

In vitro assays may optionally be employed to help identifying optimal dosage ranges, the precise dose to be employed in the formulation will also depend on the root of administration, and the seriousness of the disease or disorder, and should be decided according to the judgement of the practitioner and each patient circumstance. Effective doses may be extrapolated from dose response curves derived from in vitro animal model test systems. Preferably, the pharmaceutical composition is administered directly or in combination with an adjuvant.

The term "administered" means administration of a therapeutically effective dose of the aforementioned pharmaceutical composition comprising the compounds according to the present invention, salts and solvates thereof as defined herein to an individual.

The administration of the pharmaceutical composition can be done in a variety of ways as discussed above, including, but not limited to orally, subcutaneously, intravenously, intra-aterial, intranodal, intramedullary, intrathecal, intraventricular, intranasal, conjunctival, intrabronchial, transdermally, intrarectally, intraperitonally, intramusculary, intrapulmonary, vaginally, rectally, or intraocularly.

In still another embodiment, the present invention relates to methods of treating individuals suffering from infectious disease, cancer, tumors or other disease or disorders, comprising the step of administering to said individuals an effective amount of a pharmaceutical composition comprising a compound according to formula I or salts or solvates thereof as the active ingredient, and, optionally, a pharmaceutically acceptable carrier. In particular, the method is useful for preventing or treating infectious diseases, like viral, bacterial, parasitic or fungal infections, in particular, hepatitis B, hepatitis C, Human Immunodeficiency Virus, Herpes Virus, influenza or polyoma virus etc.

The term "halogen" refers to a fluorine, chlorine, bromine or iodine atom.

The term "$C_1$-$C_6$ alkyl" is used herein as a group or part of the group refers to a linear or branched alkyl group containing from 1 to 6 carbon atoms; examples of such groups include methyl, ethyl, propyl, isopropyl, n-butyl, isobutyl, tertbutyl, pentyl or hexyl.

The solvates may, for example, be hydrates.

The compounds according to the present invention may be composed of a spacer unit or spacer moiety as defined above, and, when n is 1 or 2, if A is a phenyl derivative or n is 1, 2 or 3 if A is a biphenyl derivative or diphenyl-alkane derivative, the spacer moiety is optionally further substituted with any one of the following substituents:

$CH_2$—Y with

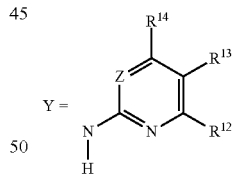
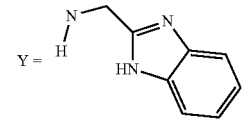

a: $Z = CH$, $R^{12} = CH_3$, $R^{13} = R^{14} = H$
b: $Z = CH$, $R^{12} = R^{14} = CH_3$, $R^{13} = H$
c: $Z = CH$, $R^{12} = C_2H_5$, $R^{13} = R^{14} = H$
d: $Z = CH$, $R^{12} = NH_2$, $R^{13} = R^{14} = H$
e: $Z = CH$, $R^{12} = R^{14} = H$, $R^{13} = CH_3$
f: $Z = CH$, $R^{12} = NHCOCH_3$, $R^{13} = R^{14} = H$
g: $Z = N$, $R^{12} = R^{14} = CH_3$, $R^{13} = H$

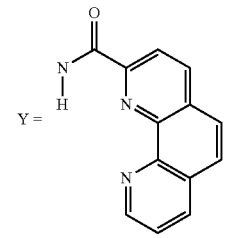

or with any one of hydrogen, $C_1$-$C_6$ alkyl group, $C_1$-$C_6$ alkoxy group, hydroxyl group or a halogen, e.g. hydrogen, methyl, ethyl, propyl or hydroxyl group.

As discussed before, the compounds according to the present invention are able to interact specifically with e.g. N-acetylneuraminic acid (Neu5Ac), the most commonly occurring sialic acid, with high affinity in highly competitive solvents. In general, the compounds according to the present invention are able to interact specifically with carbohydrate structures. In particular, said sugar molecules may be a neutral or ionic sugar residues, like an anionic or cationic sugar residue.

The compounds according to the present invention are able to mask or block the carbohydrate moieties present on the cell surface of host cells transiently or permanently. Thus, recognition, binding and subsequent invasion of the cells can be inhibited or blocked. Further, as mentioned before, the carbohydrate molecules representing the ligands of the compounds according to the present invention may be present on foreign invaders, like virus, parasites, bacteria or fungi, or may be present in proteoglycans or other glycomolecules, like glycoproteins, present in an individual.

In another embodiment, the compounds according to the present invention may be in covalent or non-covalent linkage with a further active ingredient for treating cancer.

That is, it is well known that cancer cells express different pattern of sugar molecules on the cell surface. In particular, it is well known that cancer cells express glycolipids or proteoglycanes containing e.g. Neu5Ac. Targeting anti-cancer drugs specifically to the cancer cells without affecting non-cancerous cells, is the ultimate goal in cancer therapy.

The compounds according to the present invention allow specific binding to tumor cells expressing specific types of sugar molecules which are not or only rarely expressed by non-cancerous cells. Coupling the compounds according to the present invention with anti-tumor agents enables to locate said anti-tumor agents specifically to the cancer cells. For example, said anti-tumor agents may be conveyed across the cell membranes. The skilled person is well aware of suitable compounds useful in anti-cancer therapy which may be coupled with the compounds according to the present invention.

In another embodiment, the compounds according to the present invention may be used in carbohydrates biosensors applicable in a broad field of application. For example, said biosensors may be used to determine the presence of specific types of sugar molecules indicative for specific types of diseases, specific types of microorganisms etc.

Not to be bound to theory, molecular modelling studies indicated that a compound according to the present invention incorporating three protonated 2-amino-1,8-naphthyridine units, should be able to form strong complexes with Neu5Ac through multiple interactions (see FIG. 6), including ion-pairing, neutral and charge-reinforced hydrogens bonds and CH-π-interactions.

The above mentioned non-covalent interactions should provide impetus for effective binding of Neu5Ac in aqueous media.

Furthermore, the formation of charge-reinforced hydrogen bonds between the ionic groups of 4b shown in FIG. 1 and the hydroxyl groups of neutral sugar molecules (for example, see FIG. 6c,d), should provide the major driving force for the complexation of neutral sugars in protic solvents (the binding of neutral sugars was expected to be much less effective than that of Neu5Ac). As in previously described artificial systems, the participation of the central phenyl ring of 4b in CH-π interactions with sugar CHs was expected to provide additional stabilisation of the receptor-sugar complexes.

Protonation of 2-amino-1,8-naphthyridine is feasible both at N1 and N8 positions (the protonation at N1 position produces, for example, the hydrogen-bonding surface that is complementary to that of carboxylate of Neu5Ac). According to molecular modelling both the carboxylate and the acetamido/hydroxyl of Neu5Ac should be able to participate in the binding process. Examples of hydrogen bonding motifs indicated by molecular modelling are shown in FIG. 6.

BRIEF DESCRIPTION OF THE DRAWINGS

FIG. 6 provides Examples of neutral/charge-reinforced hydrogen bonds and ion pairing found by molecular modelling studies in complexes formed between receptor 4b and (a, b, e, f) Neu5Ac or (c, d) β-D-maltose.

Figure 1:
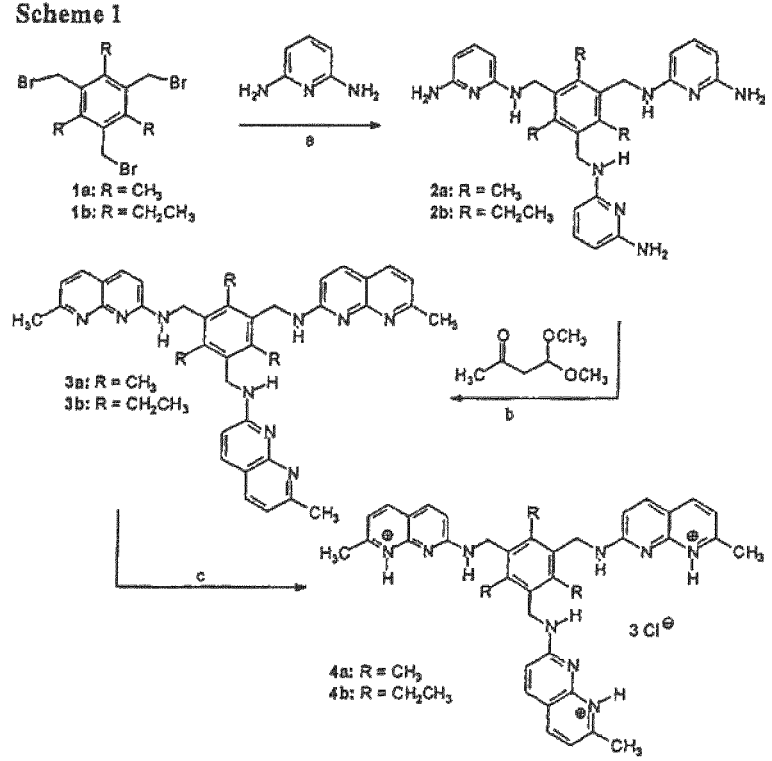
FIG. 1, scheme 1, is a scheme showing the synthesis of 1,3,5-Tris[(7-methyl-naphthyridin-2-yl)aminomethyl]-2,4, 6-trimethylbenzene (3a) and 1,3,5-Tris[(7-methyl-naphthyridin-2-yl)aminomethyl]-2,4,6-triethylbenzene (3b).
Figure 2:
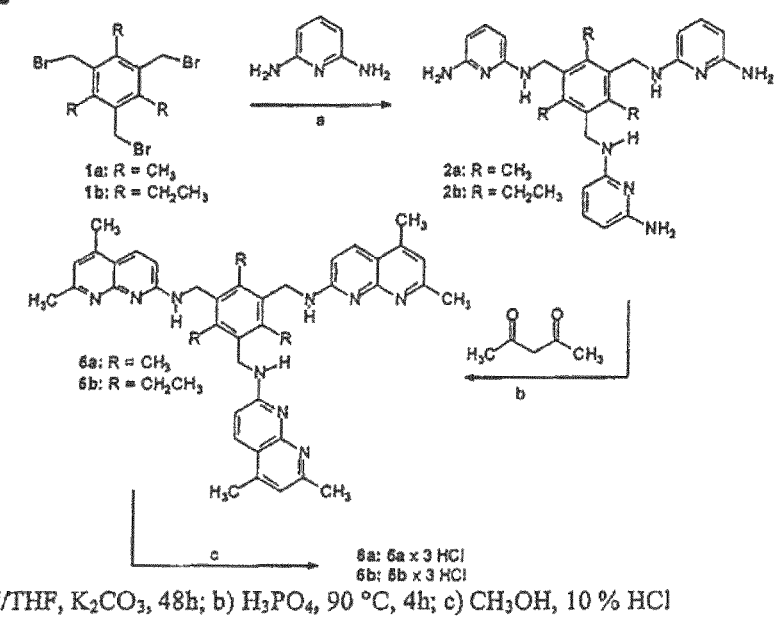
FIG. 2, scheme 2, shows the synthesis of compounds according to the present invention wherein the naphthyridine residue is substituted with $R^4$ and $R^5$ are a methyl group.
Figure 3:
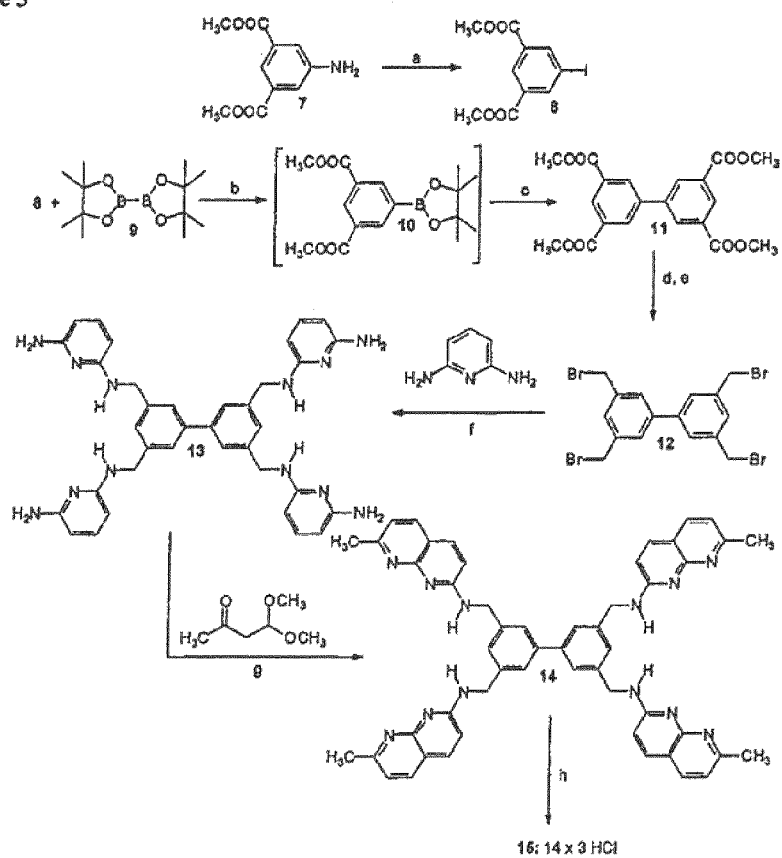
FIG. 3, scheme 3, provides a scheme of the synthesis of compounds according to the present invention wherein A is a biphenyl group, n is 4, and the naphthyridine residue is a 2 amino 1,8 naphthyridine with $R^5$ is hydrogen and $R^4$ is methyl.
Figure 4:
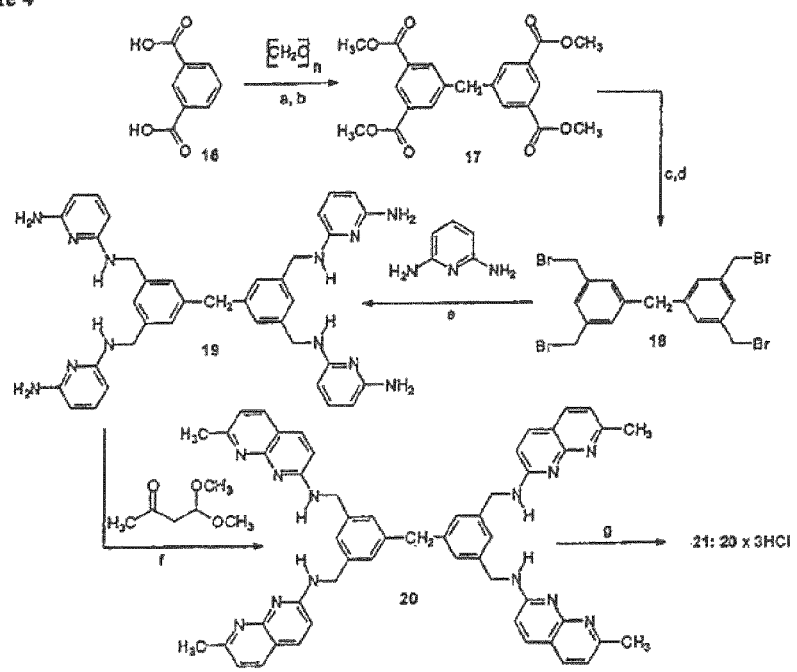
FIG. 4, shows a scheme of the synthesis of compounds according to the present invention. Therein, A is a diphenyl methane derivative, n is 4, and the naphthyridine residue is a 2 amino 1,8 naphthyridine with $R^5$ is hydrogen and $R^4$ is methyl.
Figure 5:
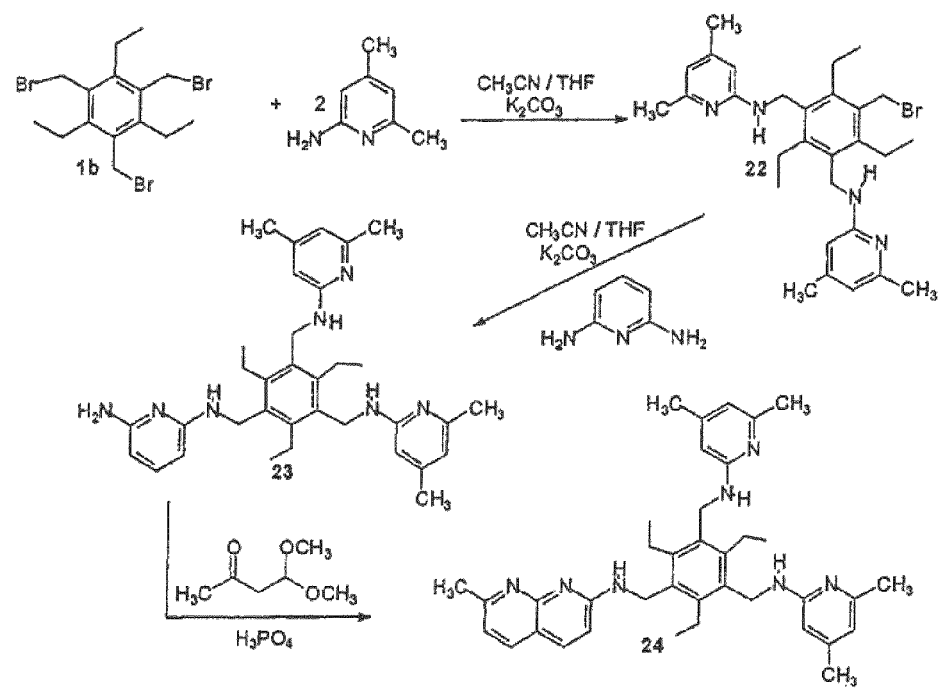
FIG. 5, scheme 5, shows the synthesis of compounds according to the present invention wherein A is a phenyl derivative wherein $R^1$, $R^2$ and $R^3$ are ethyl, n is 1.

The present invention is further described by reference to the following non-limiting figures and examples. The numbers indicated for the title compound refer to the numbering shown in FIGS. 1 to 5, respectively.

EXAMPLES 1,3,5-Tris[(6-amino-pyridin-2-yl)aminomethyl]-2,4, 6-trimethylbenzene (2a)

A mixture of 1,3,5-tris(bromomethyl)-2,4,6-trimethylbenzene (0.72 g, 1.8 mmol), 2,6-diamino-pyridine (1.20 g, 11 mmol), and $K_2CO_3$ (0.79 g) in $CH_3CN$ (100 mL) was stirred at room temperature for 24 h and then heated under reflux for 2 h. After filtration of the reaction mixture and evaporation of $CH_3CN$, the obtained powder was suspended in $CHCl_3$. The suspension was filtrated, the chloroform solution was washed several times with water, dried, and the solvent was removed under reduced pressure. The crude product was crystallized from THF/hexane. Yield 60%. M.p. 130-132° C.; $^1$H NMR (500 MHz, $CDCl_3$): δ=2.38 (s, 9H), 4.01 (t, 3H, J=4.4 Hz), 4.15 (s, 6H), 4.35 (d, 6H, J=4.4 Hz), 5.81-5.84 (m, 6H), 7.24 (d, 3H). $^{13}$C NMR (125 MHz, $CDCl_3$): δ=15.83, 41.65, 95.70, 96.81, 133.78, 136.84, 139.25, 157.68, 157.99. HR-MS calcd for $C_{27}H_{33}N_9$: 483.2859; found: 483.2867.

1,3,5-Tris[(6-amino-pyridin-2-yl)aminomethyl]-2,4, 6-triethylbenzene (2b)

A mixture of 1,3,5-tris(bromomethyl)-2,4,6-triethyl-benzene (0.79 g, 1.8 mmol), 2,6-diamino-pyridine (1.20 g, 11 mmol), and $K_2CO_3$ (0.79 g) in $CH_3CN$ (100 mL) was stirred at room temperature for 24 h and then heated under reflux for 2 h. After filtration of the reaction mixture and evaporation of $CH_3CN$, the obtained powder was suspended in $CHCl_3$. The suspension was filtrated, the chloroform solution was washed several times with water, dried, and the solvent was removed under reduced pressure. The crude product was crystallized from THF/hexane. Yield 40%. M.p. 164-165° C.; $^1$H NMR (500 MHz, $CDCl_3$): δ=1.22 (t, 9H, J=7.5 Hz), 2.75 (q, 6H, J=7.5 Hz), 4.05 (t, 3H, J=4.2 Hz), 4.20 (s, 6H), 4.35 (d, 6H, J=4.2 Hz), 5.83-5.86 (m, 6H), 7.24 (m, 3H); $^{13}$C NMR (125 MHz, $CDCl_3$): δ=16.9, 23.0, 40.6, 95.9, 96.9, 133.3, 139.4, 143.8, 157.8, 157.9; HR-MS calcd for $C_{30}H_{39}N_9$: 525.3328; found: 525.3322. $R_f$=0.21 ($CHCl_3/CH_3OH$ 7:1 v/v).

1,3,5-Tris[(7-methyl-naphthyridin-2-yl)aminomethyl]-2,4,6-trimethylbenzene (3a)

1,3,5-Tris[(6-amino-pyridin-2-yl)aminomethyl]-2,4,6-trimethylbenzene (2a) (2.0 g, 4.1 mmol), 4,4-dimethoxy-2-butanone (12.3 mmol), and $H_3PO_4$ (50 mL) were held at 90° for 4 h and then stirred at room temperature for 2 h. The reaction mixture was poured into water (200 mL), neutralized, and extracted several times with chloroform. The collected organic layers were dried over $MgSO_4$ and the solvent was removed under reduced pressure. The crude product was purified several times by column chromatography (silica gel, $CHCl_3/CH_3OH$, 7:1 to 2:1 v/v). Yield 30%. M.p. 207-208° C. $^1$H-NMR (400 MHz, $CDCl_3$): δ=2.34 (s, 9H), 2.61 (s, 9H), 4.71 (d, 6H, 3H, J=3.0 Hz), 5.12 (t, 3H, J=3.0 Hz), 6.60 (d, 3H, J=8.8 Hz), 6.98 (d, 3H, J=8.0 Hz), 7.65 (d, 3H, J=8.8 Hz), 7.74 (d, 3H, J=8.0 Hz). $^{13}$C NMR (100 MHz, $CDCl_3$): δ=15.9, 25.0, 41.1, 112.4, 114.9, 115.9, 133.3, 136.0, 136.5, 137.2, 156.5, 158.7, 161.3. HR-MS calcd for $C_{39}H_{38}N_9$: 632.3250; found: 632.3256. $R_f$=0.80 ($CHCl_3/CH_3OH$ 2:1 v/v).

1,3,5-Tris[(7-methyl-naphthyridin-2-yl)aminomethyl]-2,4,6-triethylbenzene (3b)

1,3,5-Tris[(6-amino-pyridin-2-yl)aminomethyl]-2,4,6-triethylbenzene (2b) (4.7 g, 8.9 mmol), 4,4-dimethoxy-2-butanone (26.3 mmol), and $H_3PO_4$ (50 mL) were held at 90° for 4 h and then stirred at room temperature for 2 h. The reaction mixture was poured into water (300 mL), neutralized, and extracted several times with chloroform. The collected organic layers were dried over $MgSO_4$ and the solvent was removed under reduced pressure. The crude product was purified several times by column chromatography (silica gel, $CHCl_3/CH_3OH$, 7:1 to 2:1 v/v). Yield 23%. M.p. 207-208° C. $^1$H-NMR (400 MHz, $CDCl_3$): δ=1.23 (t, 9H, J=7.5 Hz), 2.69 (s, 9H), 2.82 (q, 6H, J=7.5 Hz), 4.74 (br s, 3H), 4.82 (d, 3H, J=3.0 Hz), 6.58 (d, 3H, J=8.6 Hz), 7.04 (d, 3H, J=8.1 Hz), 7.72 (d, 3H, J=8.6 Hz), 7.79 (d, 3H, J=8.1 Hz). $^{13}$C NMR (100 MHz, $CDCl_3$): δ=16.9, 23.1, 25.3, 40.6, 112.1, 115.2, 118.3, 132.9, 136.2, 136.9, 144.5, 156.7, 158.4, 161.3. HR-MS calcd for $C_{42}H_{44}N_6$: 674.3719; found: 674.3714. $R_f$=0.89 ($CHCl_3/CH_3OH$ 2:1 v/v).

Trihydrochloride 4b

Compound 3b (0.1 g, 0.148 mmol) was dissolved in MeOH (3 mL), and HCl (1 mL, 10%) was added. The resulting solution was stirred at room temperature for 30 min and evaporated in vacuo. This procedure was repeated twice to obtain the trihydrochloride 3b. M.p. 237-238° C. $^1$H NMR (400 MHz, DMSO-$d_6$): δ=1.16 (t, 9H, J=9.9 Hz), 2.78-2.82 (s+q, 9H+6H), 4.80 (d, 3H, J=3.5 Hz), 7.33 (d, 3H, J=12.1 Hz), 7.48 (d, 3H, J=10.6 Hz), 8.15 (d, 3H, J=12.1 Hz), 8.61 (d, 3H, J=10.6 Hz), 9.08 (br s, 3H), 15.29 (br s, 3H). $^{13}$C NMR (100 MHz, DMSO-$d_6$): δ=15.9, 19.5, 22.8, 39.5, 116.1, 116.8, 117.8, 130.7, 136.2, 143.7, 149.5, 154.8, 159.5. ESI-MS: m/z=676 [M-2H$^+$]$^+$, 338.6 [M-H$^+$]$^{2+}$, 226.1 [M]$^{3+}$ ($C_{42}H_{48}N_9{}^{3+}$).

Compound 22

To a mixture of 1,3,5-tris(bromomethyl)-2,4,6-trimethyl-benzene (1b) (3.00 g, 6.80 mmol) and $K_2CO_3$ (1.88 g, 13.60 mmol) in $CH_3CN$/THF (1:1 v/v; 40 mL) was added dropwise a $CH_3CN$ (10 mL) solution of 2-amino-4,6-dimethyl-pyridine (1.66 g, 13.60 mmol). The mixture was stirred at room temperature for 72 h. After filtration and evaporation of solvents, the crude product was purified by column chromatography (ethyl acetate/toluene, 1:3 v/v). Yield 30%. M.p. 77-78° C. $^1$H-NMR (400 MHz, $CDCl_3$) δ=1.22 (t, 3H, J=7.5 Hz), 1.29 (t, 6H, J=7.5 Hz), 2.24 (s, 6H), 2.36 (s, 6H), 2.73 (q, 2H, J=7.5 Hz), 2.85 (q, 4H, J=7.5 Hz), 4.23 (t, 2H, J=4.2 Hz), 4.37 (d, 4H, J=4.2 Hz), 4.62 (s, 2H), 6.10 (s, 2H), 6.35 (s, 2H). $^{13}$C-NMR (100 MHz, $CDCl_3$) δ=16.4, 16.7, 21.1, 22.8, 23.0, 24.1, 29.6, 40.5, 103.6, 113.9, 131.9, 133.4, 143.8, 144.9, 148.9, 156.5, 158.0. HR-MS calcd for $C_{29}H_{39}BrN_4$ 5232.2353; found: 522.2360. $R_f$=0.31 (ethyl acetate/toluene, 1:3 v/v).

Compound 23

To a mixture of 2,6-diaminopyridine (0.50 g, 4.58 mmol) and $K_2CO_3$ (0.21 g, 1.53 mmol) in $CH_3CN$ (10 mL) was added a $CH_3CN$/THF (1:1 v/v; 20 mL) solution of compound 22 (0.9 g, 1.53 mmol). The mixture was heated to reflux for 12 h and stirred at room temperature for additional 24 h. After filtration and evaporation of solvents the crude product was taken up in $CHCl_3$ (20 mL) and washed several times with water. The organic phase was dried over $MgSO_4$ and the solvent was evaporated. The crude product was purified by column chromatography (toluene/ethyl acetate 1:3 (v:v) containing 2% triethylamine). Yield 62%. M.p. 78-79° C. $^1$H-NMR (400 MHz, $CDCl_3$) δ=1.23 (t, $^3$J=7.5 Hz, 9H), 2.23 (s, 6H), 2.35 (s, 6H), 2.74 (q, $^3$J=7.5 Hz, 6H), 4.01 (br. s, 1H), 4.13 (br. s, 2H), 4.18 (br. s, 2H), 4.35 (d, $^3$J=4.3 Hz, 2H), 4.37 (d, $^3$J=4.3 Hz, 4H), 5.83 (d, $^3$J=6.0 Hz, 1H), 5.85 (d, $^3$J=5.7 Hz, 1H), 6.11 (s, 2H), 6.34 (s, 2H), 7.25 (t, $^3$J=7.8 Hz, 1H). $^{13}$C-NMR (100 MHz, $CDCl_3$) δ=16.85, 21.09, 22.88, 24.21, 40.47, 40.63, 95.89, 96.67, 103.46, 113.90, 133.18, 143.53, 143.58, 139.18, 148.72, 156.76, 157.71, 157.85, 158.24. HR-MS calcd for $C_{34}H_{45}N_7$ 551.3736; found: 551.3742. $R_f$=0.3 (chloroform/methanol, 7:1 v/v)

Compound 24

Compound 23 (100 mg, 0.18 mmol), 4,4-dimethoxybutanone (0.016 mL, 0.36 mmol) and $H_3PO_4$ (5 mL) were held at 90° C. for 2.5 h and then stirred at room temperature for 2 h. The reaction mixture was poured into water (10 mL), neutralized and extracted several times with chloroform. The collected organic layers were dried over $MgSO_4$ and the solvent was removed under reduced pressure. The crude product was purified several times by column chromatography (chloroform/methanole 20:1 v/v). Yield 16.5%. $^1$H-NMR (400 MHz, $CDCl_3$)=1.23 (m, 9H), 2.23 (s, 6H), 2.34 (s, 6H), 2.72 (s, 3H), 2.80 (m, 6H), 4.26 (s, 2H), 4.37 (d, J=4.1 Hz, 4H), 4.62 (s, 1H), 4.79 (d, J=3.8 Hz, 2H), 6.11 (s, 2H), 6.35 (s, 2H), 6.60 (d, J=8.7 Hz, 1H) 7.05 (d, J=8.0 Hz, 1H), 7.72 (d, J=8.7 Hz, 1H), 7.80 (d, J=8.0 Hz, 1H).

The invention claimed is:

1. A compound of the general formula (I) including racemates, racemic-mixtures, pure enantiomers and their diasteromers, or salts or mixtures thereof

wherein

A is a spacer moiety selected from i) a phenyl derivative of the general formula (II)

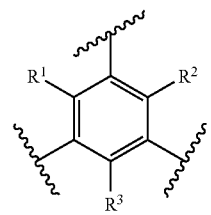

wherein each of $R^1$, $R^2$ and $R^3$ being independently a $C_1$-$C_6$ alkyl group, a $C_1$-$C_6$ alkoxy group, a hydroxyl group or a halogen;

ii) a biphenyl derivative of the general formula (III)

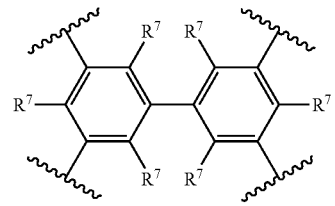

with each $R^7$ being independently a hydrogen or a $C_1$-$C_6$ alkyl group, a $C_1$-$C_6$ alkoxy group, a hydroxyl group or a halogen;

iii) a diphenyl alkane derivative of the general formula (IV)

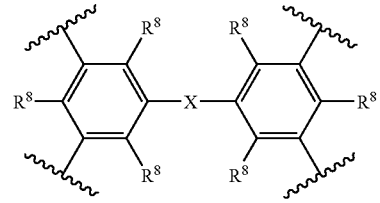

with each $R^8$ is independently a hydrogen or a $C_1$-$C_6$ alkyl group, a $C_1$-$C_6$ alkoxy group, a hydroxyl group or a halogen;

X is a $C_1$-$C_6$ alkylene group, in particular, a methylene group;

B is independently an amino-naphthyridine group of the general formula having a structure selected from the group consisting of (V), (VI), and (VII)

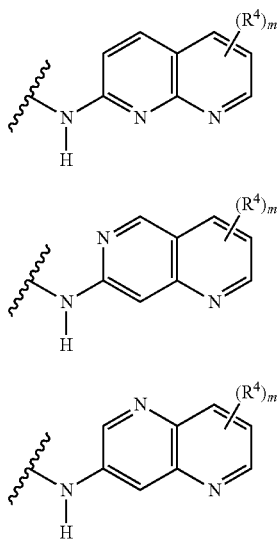

wherein each $R^4$ is independently a hydrogen, a $C_1$-$C_6$ alkyl group, hydroxyl group $C_1$-$C_6$ alkoxy group, halogen or $NR^{10}R^{11}$ with $R^{10}$ and $R^{11}$ being independently hydrogen, or a $C_1$-$C_6$ alkyl group, and m is an integer of 2 to 5, and n is an integer of 3 if A is a phenyl derivative of formula (II) or n is 4 if A is (III) or (IV).

2. The compound according to claim 1, wherein

B is an amino-naphthyridine group of the general formula having a structure selected from the group consisting of (Va), (VIa), and (VIIa)

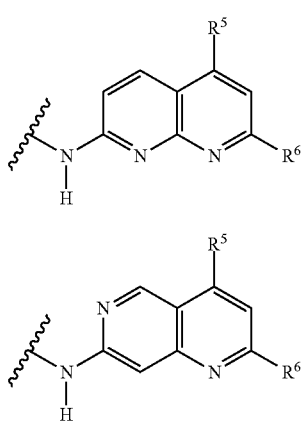

wherein $R^5$ or $R^6$ being independently hydrogen, a $C_1$-$C_6$ alkyl group, hydroxyl group, $C_1$-$C_6$ alkoxy group, halogen or $NR^{10}R^{11}$ with $R^{10}$ and $R^{11}$ being independently hydrogen, or a $C_1$-$C_6$ alkyl group.

3. The compound according to claim 1, wherein A is a phenyl derivative of the general formula II and each $R^1$, $R^2$ and $R^3$ is independently an alkyl group selected from the group consisting of methyl, ethyl, propyl and butyl.

4. The compound according to claim 3, wherein each $R^1$, $R^2$ and $R^3$ is independently a methyl or ethyl group.

5. The compound according to claim 1, wherein A is the biphenyl derivative of the general formula III and each $R^7$ is independently a hydrogen, methyl, ethyl, propyl, methoxy or ethoxy group.

6. The compound according to claim 1, wherein A is a diphenyl alkane derivative of the general formula IV and each $R^8$ is independently a hydrogen, methyl, ethyl, propyl, hydroxyl, methoxy or ethoxy groups.

7. The compound according to claim 1 wherein each $R_4$ is independently a hydrogen, or a methyl, ethyl, propyl, isopropyl or butyl group.

8. The compound according to claim 2, wherein $R_5$ or $R_6$ are independently a hydrogen or methyl, ethyl, propyl, isopropyl or butyl group.

9. The compound according to claim 2 wherein $R_6$ is methyl and $R_5$ is hydrogen or methyl.

10. The compound according to claim 1, wherein A is a phenyl derivative of the general formula II and n is 3.

11. The compound according to claim 1 wherein A is a biphenyl derivative of the general formula III or a diphenyl alkane derivative of the general formula IV wherein n is 4.

12. The compound according to claim 1 in the form of a halogen salt.

13. Pharmaceutical composition comprising a compound according to claim 1 and, optionally, a pharmaceutically acceptable carrier or excipient.

14. The compound according to claim 1, wherein X is a methylene group.

15. The compound according to claim 6, wherein each $R^8$ is a methyl group.

* * * * *